United States Patent [19]

Kuhl et al.

[11] 3,970,853

[45] July 20, 1976

[54] TRANSVERSE SECTION RADIONUCLIDE SCANNING SYSTEM

[75] Inventors: David E. Kuhl, Rosemont; Roy Q. Edwards, Plymouth Township, both of Pa.

[73] Assignee: The United States of America as represented by the United States Energy Research and Development Administration, Washington, D.C.

[22] Filed: June 10, 1975

[21] Appl. No.: 585,625

[52] U.S. Cl. ........................... 250/363 S; 250/445 T
[51] Int. Cl.² ........................................... G01T 1/20
[58] Field of Search ...................... 250/363 S, 445 T

[56] References Cited
UNITED STATES PATENTS

| | | | |
|---|---|---|---|
| 3,432,660 | 3/1969 | Anger | 250/363 S |
| 3,899,675 | 8/1975 | Floyd | 250/363 S |

*Primary Examiner*—Davis L. Willis
*Attorney, Agent, or Firm*—Dean E. Carlson; Leonard Belkin; Cornell D. Cornish

[57] ABSTRACT

This invention provides a transverse section radionuclide scanning system for high-sensitivity quantification of brain radioactivity in cross-section picture format in order to permit accurate assessment of regional brain function localized in three-dimensions. High sensitivity crucially depends on overcoming the heretofore known raster type scanning, which requires back and forth detector movement involving dead-time or partial enclosure of the scan field. Accordingly, this invention provides a detector array having no back and forth movement by interlaced detectors that enclose the scan field and rotate as an integral unit around one axis of rotation in a slip ring that continuously transmits the detector data by means of laser emitting diodes, with the advantages that increased amounts of data can be continuously collected, processed and displayed with increased sensitivity according to a suitable computer program.

5 Claims, 11 Drawing Figures

3,970,853

TRANSVERSE SECTION RADIONUCLIDE SCANNING SYSTEM

STATEMENT OF GOVERNMENT INTEREST

This invention was made in the course of, or under a contract with the U.S. Energy Research and Development Administration, or its predecessor, the U.S. Atomic Energy Commission.

BACKGROUND OF THE INVENTION

In the field of medical diagnosis and treatment of humans, it is desirable to provide an in vivo transverse section radio-nuclide scanning system. One such system, known as the Mark III scanner at the University of Pennsylvania is described in Radiology, Vol. 96, No. 3, pages 563–570, September 1970. In the described system there is provided a device for rectilinear and transverse section scanning of a human brain using an absorbed short-lived radionuclide, such as $^{99m}Tc_{43}$ pertechnetate, having four detectors for viewing four different aspects of the brain simultaneously without moving the human patient, and a self-contained computer for controlling the display and the automatic operations while minimizing processing delays. This system, however, was limited in the sensitivity it could achieve because it required the discrete, alternate periodic biasing of selected detectors back and forth in different directions in a sequence of stepped, linear, transverse detector motions that alternated periodically back and forth with six 15° rotations of the detectors to cause the four detectors to survey the entire circumference of the head through 360°, as illustrated in FIG. 5 of the cited publication.

SUMMARY OF THE INVENTION

This invention avoids the alternating direction detector movements known heretofore and obtains increased sensitivity, as well as decreased total patient scanning time, in a transverse section radionuclide scanning system for in vivo medical diagnosis of the human brain by rotating a picture frame of detectors that completely enclose the scanfield around a single axis of rotation in a slip ring. It is also advantageous continuously to transmit the detector data by means of laser emitting diodes with the advantage that the data can be continuously collected, processed and displayed with high sensitivity according to a suitable computer program. It is still further advantageous to provide a reduction of data from multiple large detectors that are offset and interlaced for improved spatial resolution without detector translation. Still further, it is advantageous to provide improved detail and reduced noise, as well as continuous operator monitoring and control. With the proper selection of elements and their arrangement, as described in more detail hereinafter, the desired continuous rotation, transmission, collection, processing and display is achieved.

OBJECTS OF THE INVENTION

It is an object of this invention, therefore, to provide an improved transverse section radionuclide scanning system that rotates a picture frame of offset and interlaced detectors that completely enclose the scan field around a single axis, and continuously transmits, collects, processes and displays the data transmitted from the detectors.

BRIEF DESCRIPTION OF THE DRAWINGS

FIG. 3a is an enlarged view of one of the detector elements of the detector assembly of FIG. 1;

FIG. 3b is a partial cross-section of the detector element of FIG. 3a;

DESCRIPTION OF THE PREFERRED EMBODIMENT

Referring to the above-cited publication, conventional electronic systems operated by suitable computer programs are known for quantification of brain radioactivity in cross-section picture format in order to permit assessment of regional brain function localized in three dimensions. In this regard it is known that the high energy radiation from short-lived radionuclides absorbed in the human brain can be detected by radionuclide detectors to produce data for collection, processing and display by the electronic system, whereby the data corresponds spatially with the location of the radioactivity sources and quantitatively with the intensity of the radiation emanating from the source in a transverse plane. One detector is described in the cited publication as a NaI (Tl) crystal detector optically coupled to a plastic light pipe including a selected Multiplier Photo Tube for converting the light pulses into electrical signal data for collection, processing and display. Detection of the radiation for the production of the required electrical signal data for the electronic system is based upon the fact that all the radiation detected emanates from fixed sources in the brain, and the intensity of the sources corresponds to the intensity of the radiation released thereby, whereby detection of the radiation quantifies the spatial location and intensity of the sources. The invention hereinafter described utilizes detectors and an electronic processing system of this type in which the detectors are continuously rotated around a single axis in a single transverse plane relative to the patient's head.

In order to explain how the method and apparatus of this invention accomplish the function of continuously rotating the detectors around one axis of rotation and continuously transmitting the required data to the electronic system, reference is made to the figures, which show an axle for continuously rotating detectors of the type described to produce the required data in the form of light pulses, and a system, comprising a data reduction package, an infrared transmitter module, and an optical transmission means for transmitting the required data to the electronic system. To this end, the axle rotates detectors that produce light pulses that are converted into electrical signal data, and these data are converted back again into light signal data so that the latter is transmitted into an electronic system, having provision for collection, processing and display in the electronic system as understood in the art from this description.

Figure 1:
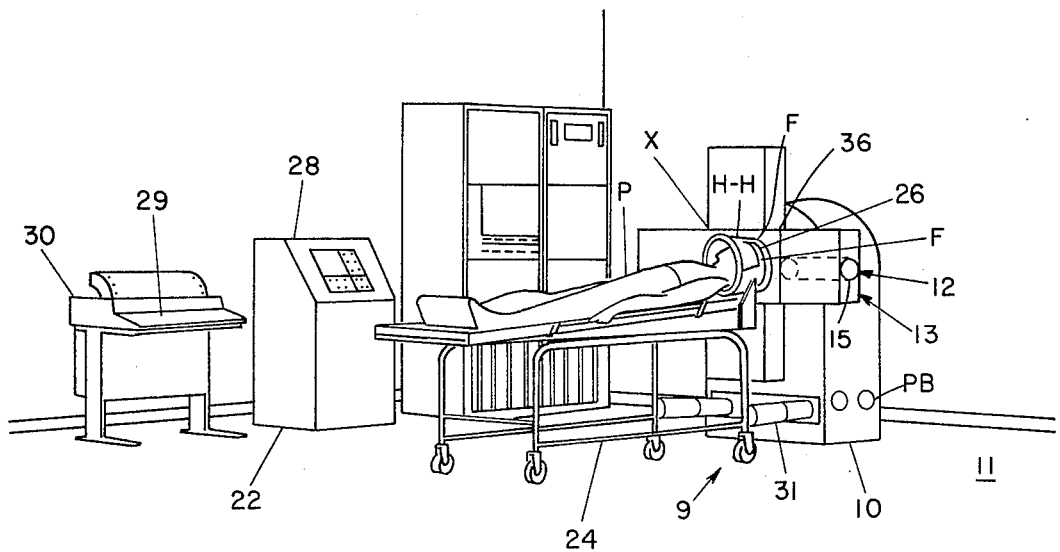
FIG. 1 is a partial three-dimensional view of the overall system of this invention.
Figure 2:
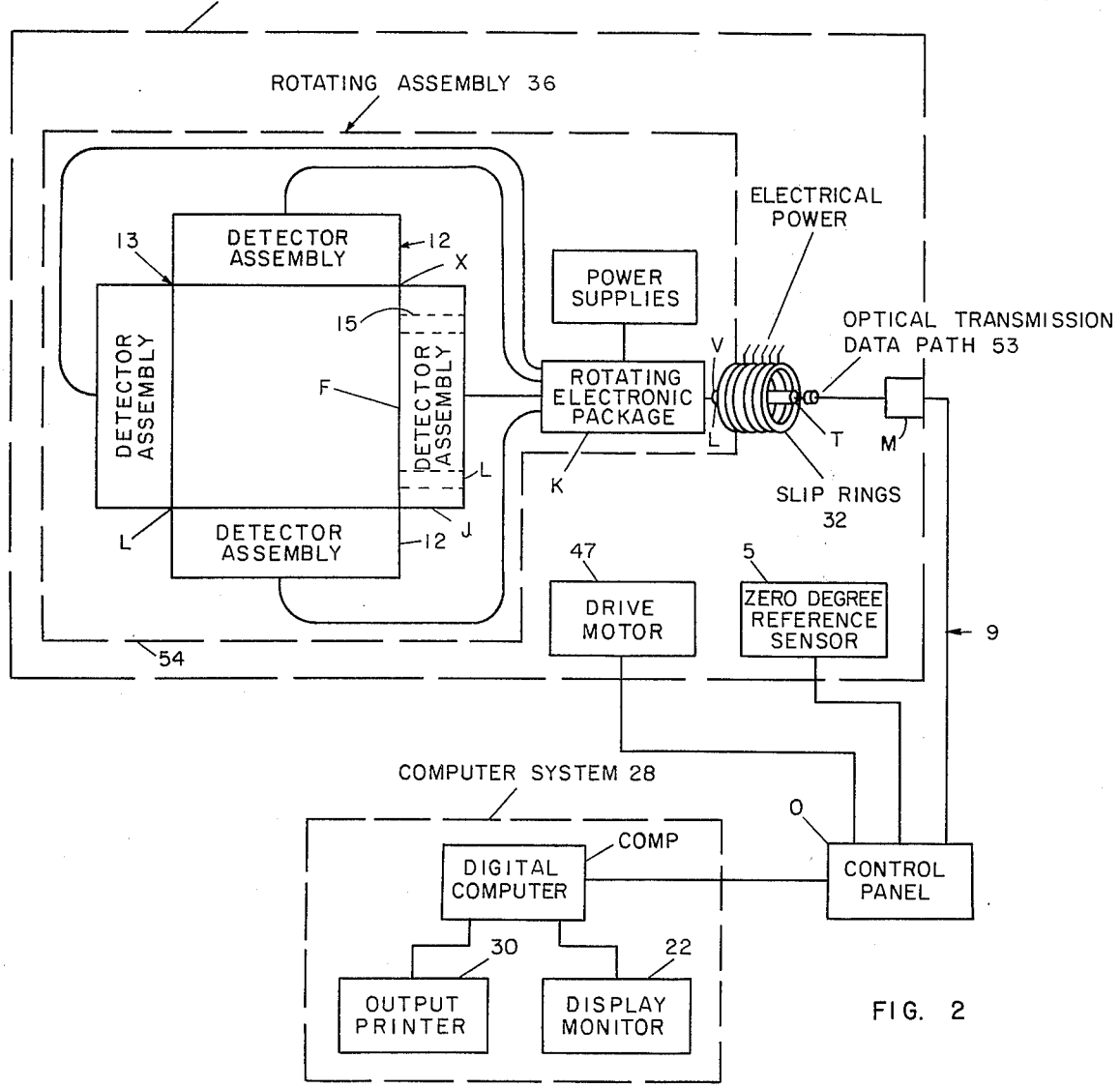
FIG. 2 is a schematic drawing of the detector system of FIG. 1.

Referring now more particularly to FIG. 1, there is shown a partial isometric view of one embodiment of this invention for providing high-sensitivity quantification of brain radioactivity in a cross-sectional scan field F, such as shown in FIG. 2, having a picture format in order to permit accurate assessment of regional brain function localized in three-dimensions. This figure illustrates the main frame 10, which is supported on floor 11, and four detector assemblies 12 for continuously rotating the whole detector assembly 13, which is arranged in a continuously rotating picture frame arrangement containing the rotating electronic package for continuously transmitting the data from each detector 15 for continuously collecting, processing and displaying the data on a conventional display monitor 22 according to a suitable computer program so that the desired high sensitivity is achieved. The conventional apparatus shown, comprises a patient liter 24 for maintaining in a head holder HH the patient's head containing the radioactive sources at fixed locations in a stationary horizontal position, while the four detector assemblies 12 continuously rotate in a transverse plane 26 that is normal to the longitudinal axis of the patient from head to foot. A conventional processing electronic system 28, comprising a suitable mini-computer having a remote computer, a conventional display monitor, and an input-output teletype 29 and printer 30 are shown for controlling the transmission of data from the rotating detector assemblies 12, and controlling the continuous processing and display thereof. While the liter 24 is conventional, it will be understood that it is attached to the main frame 10 of the embodiment 9 of FIG. 1 by a pair of conventional motor driven linear actuators 31 having push button controls PB for positioning the patient's head in the desired scanning field F at the desired level relative to the fixed transverse scanning plane produced by the continuously rotating detector assemblies 12 of this invention. FIG. 2 is a schematic drawing of the scan field F that illustrates the slip ring 32 in which the whole detector system 13, comprising the four detector assemblies 12 continuously rotates, and FIG. 2 also illustrates the electronic package K, infrared transmitter module V and the optical transmission path T for continuously transmitting the data from the detectors 15 through the slip ring 32 so that the data is continuously collected, processed and displayed according to the computer program in the conventional processing electronics 28 for providing a high-sensitivity quantification of the detected radioactivity. Conventional electrical connections from an infrared receiver module, the rotation motor 47, and the 0° reference sensor S are terminated in the control panel O, which is described in more detail hereinafter.

Figures 3A, 3B:
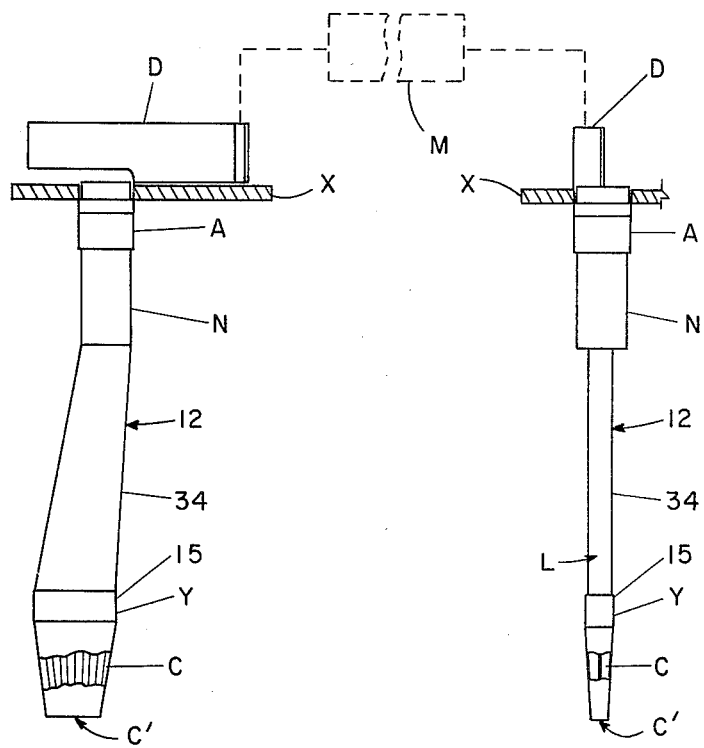

To provide high sensitivity in the embodiment 9 of FIGS. 1 and 2, an offset and interlaced system 36 of relatively large detectors is provided, and two views thereof at right angles to each other are shown in FIGS. 3a and 3b.

The tomographic scanner illustrated in the FIGS. provides representative output information regarding the radioisotope distribution in the scanned anatomical transverse section plane, wherein the isotope concentration contains significant information relating to the patient P's physiology and/or anatomy by using an isotope administered to the patient by intravenous injection, inhalation, or oral ingestion prior to the tomographic scanning process. To this end, the cross-sectional level of the patient to be examined is positioned approximately under the detectors of the scanner by biasing the liter 24 to the approximate position.

FIGS. 3a and 3b are partial cross-sectional views at right angles to each of the apparatus of this invention for locating large, accurate and sensitive commercial detectors 15 in close proximity to each other, so that the radiation emitted from the patient P in the form of gamma ray photons is sensed by the four detector assemblies 12, which are shown in quadrature in FIG. 2, and wherein each detector assembly consists of eight independent detectors 15 mounted colinearly to form a line L of detectors tangential to the scan field F shown in FIG. 2.

Referring to FIG. 3a, the collimators C, which restrict the area of the scan field F (i.e., in the transverse section plane 26 of interest) from which the gamma ray photons are accepted by each detector 15, are conventional. As a result of this collimation only gamma photons originating within relatively narrow columns C' arrive at the scintillation crystal of detectors 15. The crystal produces faint light pulses from each absorbed photon, and this light energy is collected by a light pipe 34 for transmission to a conventional photomultiplier tube N, which converts the light energy into an electrical pulse whose integral is exactly representative of the energy amplitude intensity of the initial gamma photon. However, in accordance with this invention, each light pipe 34 is offset relative to its neighboring light pipe, and tapered from a narrow cross-section to a wider cross-section, as shown in FIG. 3a, so that large detectors can be used close together.

The electrical pulse is thereupon carried to a pulse amplifier A and a discriminator module D that shapes and amplifies the electrical pulse and compares its peak level to a high and low threshold in the individual detector assembly 12. If the electrical pulse is between the high and low threshold limits, the detector assembly 12 delivers a digital output pulse to the rotating electronic package K signifying that one gamma photon of the selected energy level originating from within the narrow column C' of the scan field F, has been detected. The offset between the adjacent light pipes allows the detector elements to be placed in juxtaposition, and also allows the use of photomultiplier tubes with photocathodes of larger diameter than the center to center distance of the crystals Y, thus facilitating increased optical energy transfer from the crystal exit window to the photomultiplier cathode, and this increases the overall sensitivity of the apparatus of this invention over the systems known heretofore. After conversion into electrical digital output pulses, these pulses are converted to exactly corresponding light pulses in converter V for transmission through light pipe subsystem T in axle X to the main electronic system 28 having an infrared received module M for conversion back again to electrical signals for collection and processing in the usual manner and continuous display by the display monitor 22.

Figure 3C:
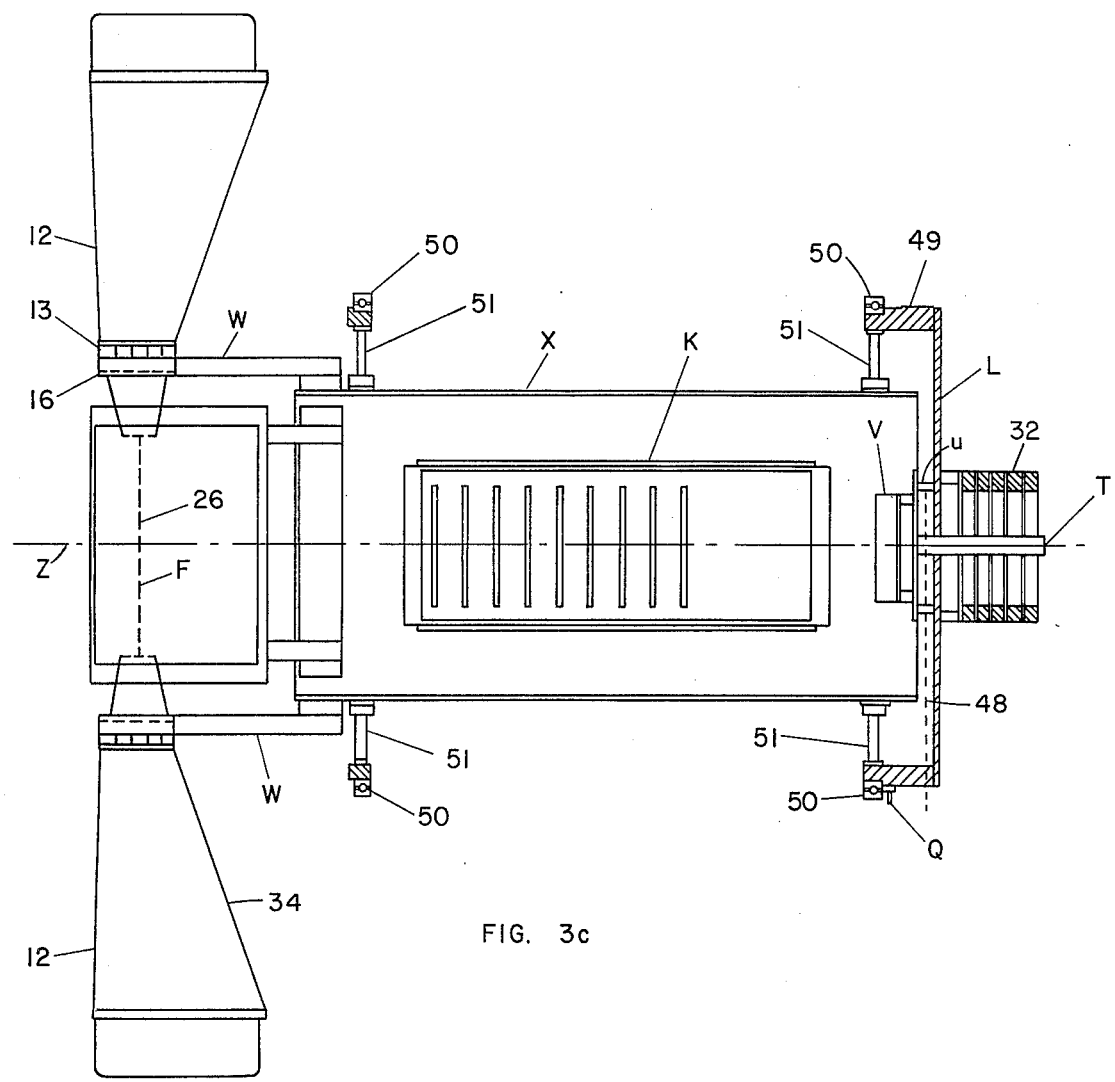
FIG. 3c is a partial cross-section of the embodiment of FIG. 1 taken along a horizontal plane.

FIG. 3c is a partial horizontal cross-section of the offset and interlaced detector apparatus of FIGS. 3a and 3b showing two of the four detector assemblies 12 and the four bearings 50 for continuously rotating the whole detector assembly 13 around a single z axis of rotation, which passes through the light pipe subsystem T for continuously receiving and transmitting the data produced by the detectors for the conventional processing and display apparatus of FIG. 1. As illustrated in FIG. 3c, the continuously rotable detector assemblies have tapered light pipes 34 that are rigidly mounted for rotation on struts 51 and mounting arms W, which are connected to the continuously rotable cylindrical axle X that contains the electronics for receiving and transmitting the detector data to the processing and display apparatus of FIG. 1 through the light pipe subsystem T of FIG. 2. The square axle X is centered to rotate the detector assembly 13 along the Z axis that passes through the light pipe subsystem T. To this end, the four detector assemblies 12 are attached by mounting arms u to the square axle X, and the axle is positioned by struts 51 within the large diameter antifriction bearings 50. The slip rings 32 and the infrared emitting subassembly module V are supported from a plate L which is fastened to a timing belt sprocket 49 that receives the rotary drive through the timing belt 48, as understood from FIG. 3d. The rotating data reduction electronic package K has the control panel O mounted on the opposite side, while an optical vane Q provides 0° position reference sensor S.

Figure 3E:
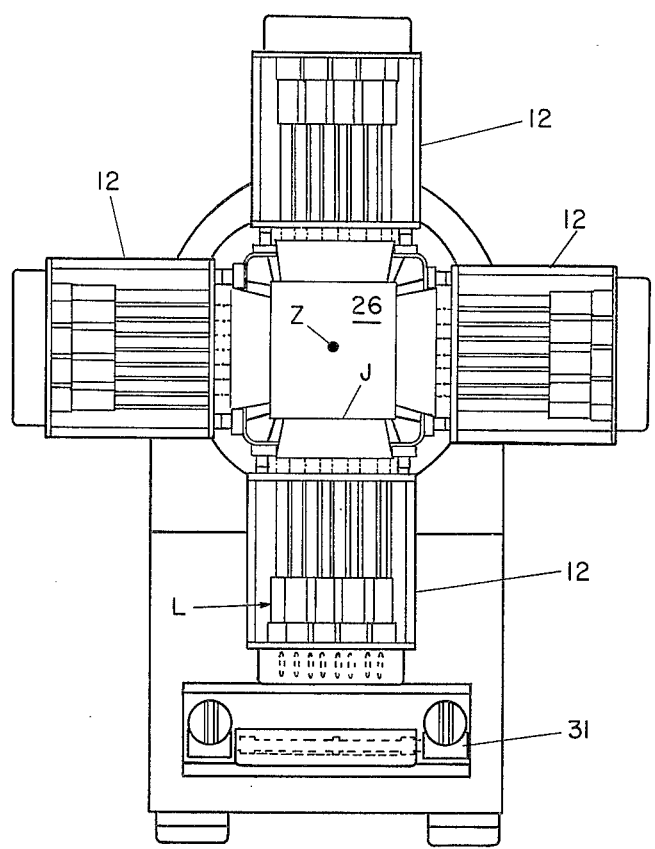
FIG. 3e is a partial cross-section and end-view of the apparatus of FIG. 3d taken along the transverse direction plane of this invention that is normal to the planes of FIGS. 3c and 3d.
Figure 3D:
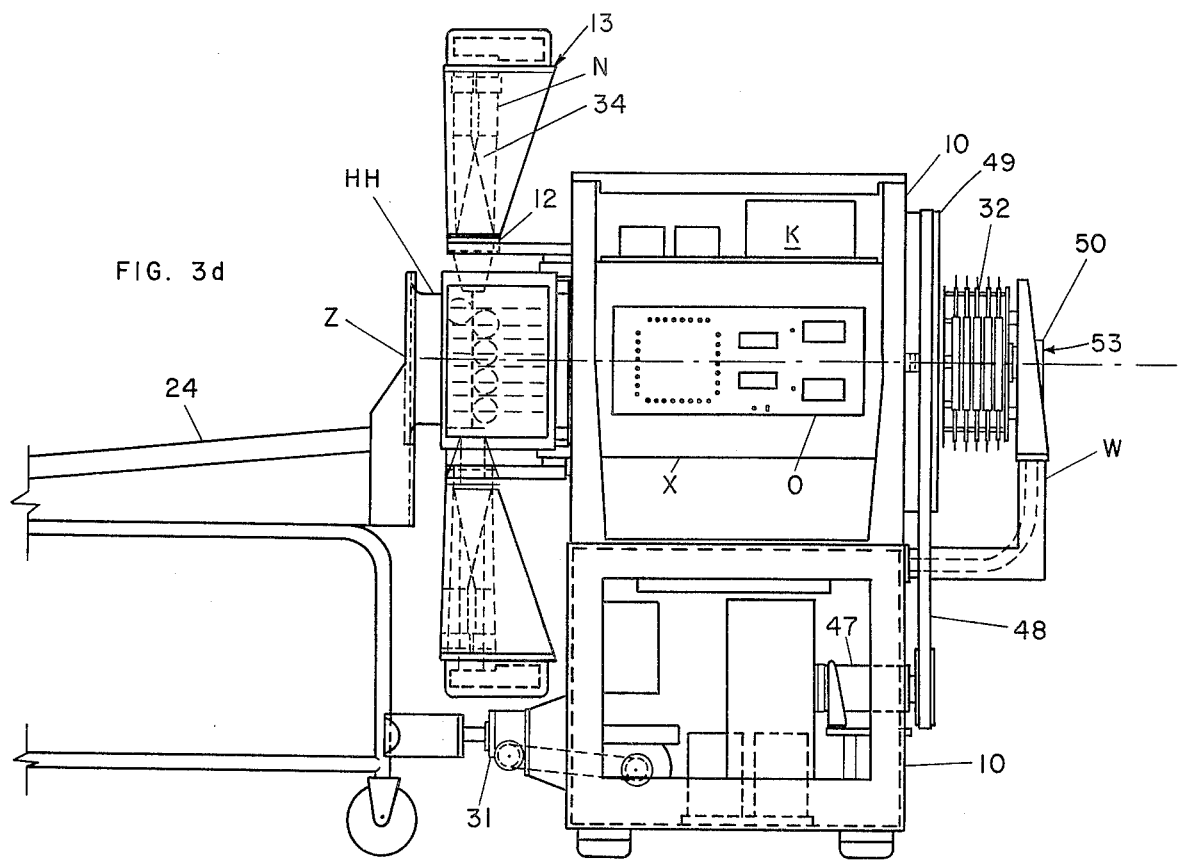
FIG. 3d is a partial cross-section of the apparatus of FIG. 3c taken along a vertical plane at right angles to the plane of FIG. 3c.

The main frame 10 of the apparatus of embodiment 9 is shown in FIG. 3d. The four detector assemblies 12 are mounted on the large hollow square axle X so that the axle encloses the data reduction electronic package K. Mounted on one side of the axle is the control panel O. The rear end of the axle contains the electrical power for the rotating electronics, thereby enabling them to rotate continuously. Also, on the Z axis at the rear end thereof is an infrared emitting module V that is provided with electro-optical communication channels 53 over which the data derived by the detectors is transmitted to the processing electronics 28.

FIG. 3d, which is a cross-section of FIG. 3c along the Z axis thereof shows the motor 47, which is mounted on the frame 10, for driving the rotable detector system 13 through endless belt 48 that rotates sprocket 49, which is mounted on a bearing 50 at the end of an arm 51 on the frame 10 that holds the slip ring 32. This slip ring transmits the electrical power required to operate the detectors in detector assemblies 12, and also the power required to operate the described electronic package K that rotates with the detector assemblies 12 for converting the electrical signals from the detector assemblies 12 back into light pulses again for transmission to the main electronic system 28 through the 32 optical data channels 53 corresponding to the 32 detectors along the center of the slip ring, as shown in FIG. 2. As shown in FIG. 2 and FIG. 3e, which is a cross-section of FIG. 3d in the transverse plane of rotation of this invention, the rotatable assembly, which is defined in FIG. 2 by the dashed line 54, contains four detector assemblies 12 that are connected to the rotating electronic package K, and the infrared transmitter module V for transmission of the required data in the form of light pulses that are carried to the main electronic system 28 by the described optical data channels 53, FIGS. 3d and 3e show orthogonal views of the connection between the motor 47 and the liter 24 for biasing the liter back and forth in small incremental steps to change the level of the transverse plane 26 that is scanned by the rotating detector assemblies 12.

Figure 4:
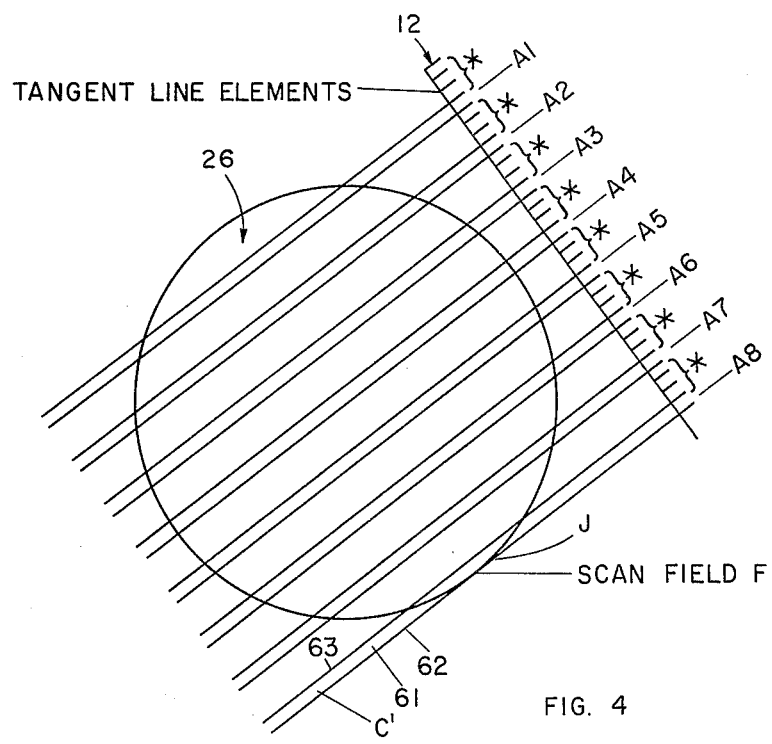
FIG. 4 is a partial cross-section of the transverse section scanned by the apparatus of FIG. 3b in general and the "A" detectors thereof in particular.

As shown in FIG. 4, which illustrates the scan of one detector assembly 12 at one point of time, the detector portions are numbered or starred depending on their location and response. Thus, for example, eight detectors A1 – A8 are responsive during the specified point in time to detect the photons emanating in the transverse plane 26 along the path 61 between the respective scan boundary lines 62 and 63, while the starred "A" detector portions which are in between the active detector portions, are not responsive, i.e., the starred detector portions are inactive.

Since eight detectors are included in each detector assembly 12, the scan field F is partially surveyed by eight narrow columns C' of sensitivity to gamma photon origin. The width of these columns C' of sensitivity is controlled by the geometry of the design of the collimators C and at the focal point of the collimator, approximately one quarter of the axial spacing of the adjacent detectors. For simplification purposes of mathematical analysis and data processing, these Columns C' of sensitivity are of uniform width and terminate at a line tangential to the circular scan field. The width of this column at the tangent line J is referred to as the tangent element. This relationship of a single detector assembly to the scan field F is diagramed in FIG. 4. Thus, it will be understood that each detector assembly provides sensitivity to only one fourth of the scan field, since the space between the columns C' of sensitivity are not "seen" by the detector assembly. When a point in the scan field is covered by columns of sensitivity form all tangent lines by their continuous rotation, the point is surrounded by a finite circular area that represents the minimum spatial resolution of the scanner.

Figure 5:
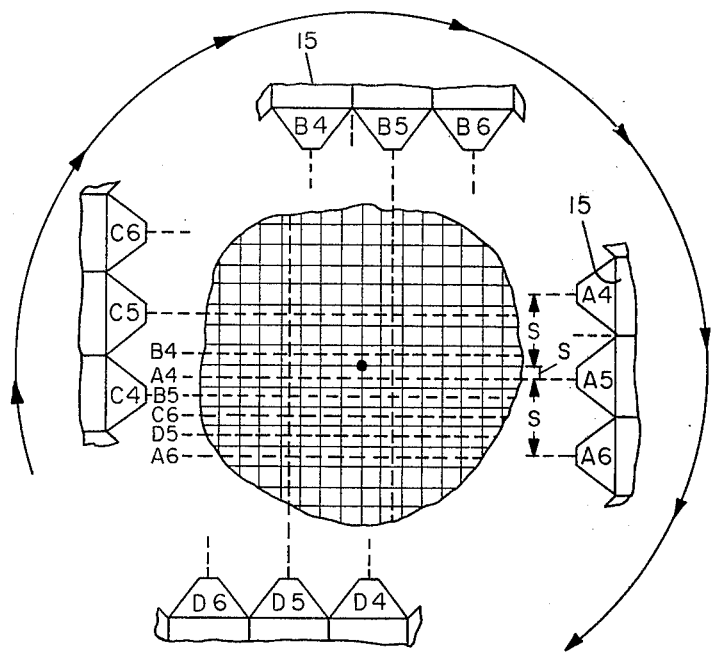
FIG. 5 is still another schematic view of the transverse section scanned by the apparatus of FIG. 3b.

As shown in FIG. 5 the detectors 15 in the opposite detector assemblies A and B and C and D respectively are offset from each other and they rotate in fixed relation to each other, such that each detector in the one assembly scans the space between the detectors in its oppositely facing detector assembly. Therefore, by rotating the offset detectors in each opposite assembly the respective scans are interlaced with respect to each other in the opposite assemblies so that a large amount of data is rapidly and continuously produced for quantifying the brain radioactivity in cross-section picture format in order to permit an accurate assessment of the regional brain function localized in three dimensions and with a high sensitivity that was not possible with the apparatus known heretofore.

By providing four detector assemblies 12, each offset one fourth of the distance of the individual detector spacing with respect to the scan field axis Z, and an axle X for rotating them successively into a stated tangent line position, a total of 32 columns C' of sensitivity normal to the tangent line J are provided. This interlacing process is diagramed in FIG. 5. In order to satisfy the requirements of the data processing algorithm for the reconstruction of the isotope distribution in the cross-sectional plane (i.e., the scan field F), data must be collected at tangent lines J completely surrounding the scan field F at relatively small angular intervals. The described system of this invention, in one sequence, thus provides for collecting data comprising 32 tangent elements at any degree intervals.

Figure 6:
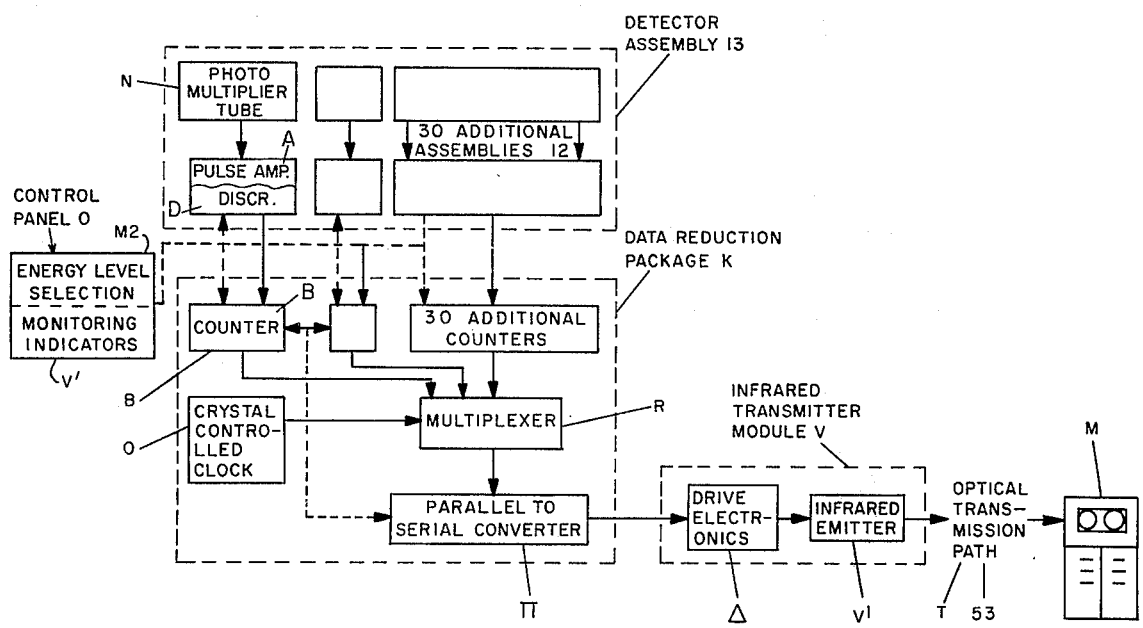
FIG. 6 is a partial schematic view of the transmission system of FIG.'s 1 and 2.

A block diagram of the electronic functions of the rotating electronics is contained in FIG. 6. The output pulses from the photomulplier tubes N, if they fall within the energy level window (i.e., upper and lower amplitude limits) established by the control panel O, are converted into standardized digital pulses by pulse amplifier module A and discriminator module D mounted in the detector assemblies 12. These digital pulses are fed to thirty-two counters contained in the electronic data reduction package K. The counters B accumulate the detected counts from each detector channel, and the crystal clock θ initiates periodic serial digital words that are transmitted over the optical data channels 53 in optical transmission path T. Each of the words causes the incremental drive motor 47 to move the rotating axle X and the detector assemblies 12 at any fraction of 1°. For example, when the contents of the rotating structure has moved 2.5 degrees, the contents of the counters are successively selected by the multiplexer R to be transferred to the parallel-to-serial converter Π and reset. The binary value of these accumulated counts are then included in the periodic serial output words transmitted over the optical data channels 53. Various auxiliary electronic equipment understood in the art, such as power suppliers, monitoring devices, controls, etc., (Δ, V', M2) are also contained in the rotating axle X.

Figure 7:
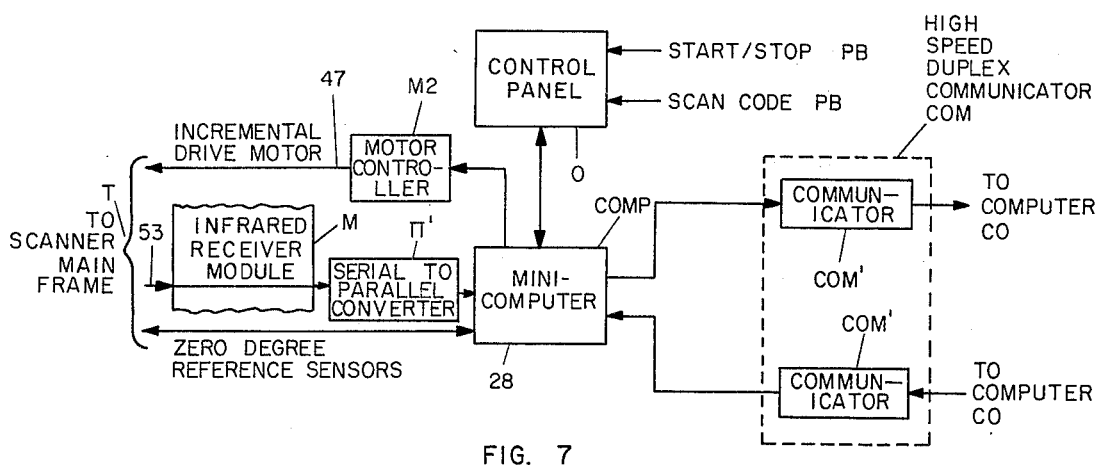
FIG. 7 is a partial schematic view of the computer control system of FIG. 1.

A block diagram of the control panel O is shown in FIG. 7. The principal component is a digital minicomputer COMP. Control of the rotation, data buffer storage and data preprocessing are functions performed. Information received from the 0° reference sensor δ enables synchronization of the rotational position with the data collection. Certain control and monitoring display functions not necessarily required for an understanding of the rotation features of this invention are contained on the console control panel, such as, a "computer ready" light (not shown) a "start scan" push button PB, an "abort scan" push button (not shown), a revolution counter (not shown), and scan identifying number entry thumb wheels (not shown). The mini-computer senses, enters and outputs the desired information to these devices, and the control panel communicates with a main remote computer CO located in another room over two co-axial cables (not shown) carrying high speed serial digital words in each direction.

In operation, the patient P on the liter 24 is manually moved into the position where the liter connects to the linear actuators 31 and the patient's head is positioned thereby at the desired level in the head holder HH relative to the plane of the transverse scanning field F, which is fixed by the continuous rotation of the detector assemblies 12 around axis Z. Thereupon, the detectors 15 receive the gamma photons from the fixed radionuclide sources in the patient's head, and the NaI crystals Y in the detectors 15 produce light pulses for each photon received so that the light pulses are amplified by the photomultipliers to produce electrical signals whose presence corresponds to the tangential data employed heretofore for displaying the spatial location and intensity of the sources. These electrical output signals, if they fall within the energy level window limits set on the control panel, are converted into standardized digital pulses by the pulse amplifier A and discriminator modules D mounted in the detector assemblies 12, and these digital pulses are fed to the 32 counters B contained in the data reduction package K. These counters B accumulate the detected counts from each detector channel, and the crystal clock θ initiates periodic serial removal of the accumulated detected counts in the form of serial digital words. Each word causes the drive motor 47 to rotate the detector assemblies a small fraction of 1° around the Z axis and, when this rotation equals 2.5°, the contents of the counters are successively selected by the multiplexer R and transferred to the parallel-to-serial converter Π and reset. The binary value of these accumulated counts are then converted to light pulses by the laser photoemitter diodes in infrared emitter V' for transmission as periodic serial output words over the optical data channels 53 in optical transmission path T.

The tangential data contained in these light pulses and words, is received and converted in the infrared receiver module M and transferred through a conventional serial-to-parallel converter Π' to the mini-computer, COMP, which is under the control of the operator through the control panel O, for sending its output data to the remote computer CO through communicators COM, for receiving input data from the remote computer through the conventional communicators, while the control of the rotation, the data buffer storage, and the data processing are under the control of the control panel, as is understood in the art, so that the information received from the zero degree reference sensor enables synchronization of the rotational position of the detector assemblies with the data collection and processing in a conventional manner.

For example, the tangential data obtained from the detector assemblies through the described system is processed to form a reconstructed matrix of radionuclide distribution in the following manner. First a preprocessor in the computer CO accumulates the count data recorded by each detector for the duration of the scan time. This preprocessor batches the 2.5° rotation output data into 7.5° output increments. The detector assemblies 12 continuously rotate a preset number of times at a predetermined constant number of revolutions per minute unless terminated before by hand by the operator of the control panel O. After each revolution, the accumulated data is transferred to the remote digital computer in the proper format, and the computer program generates a 64 by 64 element data matrix that is corrected by each incoming tangent line of data in such a way that a scan of the matrix at a particular angle produces tangent line values equal to the collected tangent line values at that angle. This program utilizes a conventional additive correction technique understood in the art in which the differences between the matrix data values and the associated tangent values are added to the matrix data.

The operation of the described program is performed on each 7.5 output angle increment in an orthogonal sequence. When this process is completed for one rotation of the detector assemblies 12, the matrix data is sent as an output to the display monitor system for storing in a disc memory in the remote computer CO. The program is completed in 30 seconds, after which it awaits updated tangent data from the preprocessor in order to correct the matrix data to agree with the new set of tangent data.

When the detector assemblies of this embodiment have completed the desired number of rotations and all of the data has been processed, the reconstructed matrix, which is stored in the disc memory, is sent to the display system. Upon operator request, a curve of any data line in the reconstructed matrix may be generated and sent to the printer 30. The operator may also request a quantitative printout of any part or all of the reconstructed matrix data.

While the above has described a tomographic scanner for the head, anatomical areas other than the human head can be accessed in a modification of the described apparatus and method by employing a larger hollow axle of greater dimensions than required for the described head scanning, and locating the processing electronics on the exterior so that the patient's body can pass through and be positioned in the axle. In this case, a greater or lesser number of detector elements could be used in each detector assembly, depending on the diameter of the scan field, and the spatial resolution desired.

In a further modification, the eight discrete detector scintillation crystals in each detector assembly are replaced with a single long crystal bar and fewer photomultiplier tubes using standard techniques for achieving spatial resolution by signal comparison.

In still another modification, the scintillation detectors are replaced with other types of detectors, such as, the solid state germanium type having conventional electronics well known in the art.

It is understood that a quantity of detector assemblies other than four (at least three) can be used by forming them into an appropriate closed polygonal configuration. Likewise, numerous algorithms known in the art can be used in the remote computer.

The following is an example of the embodiment of FIG. 1:

EXAMPLE I

In one Example, using 32 collimated NaI (Tl) crystal (3 inches high 1 inch wide, 1 inch thick) arranged 8 on a side as a continuous box about the head for detection of 140 keV gamma rays (from $^{99m}Tc$), each detector is offset on a side by ¼ inch compared to its corresponding detector on the opposite side, and all four sides, which completely enclose the scan field in a detector picture frame, contribute data to any angular view of the head. By interlacing their lines of view at any rotation angle, each tangent line of data is caused to contain 32 tangent elements, each ¼ inch long, improving the resolution possible with this configuration, even though only 8 detectors are used on each side of the detector frame. This permits good resolution even though there is no linear translation of the individual detectors.

The four detector assemblies, in the detector picture frame are driven as an integral unit at a constant rpm collecting one frame of data per revolution and adding frames for the required statistical content of the scan.

The transverse scan is made in a simple mechanical arrangement with discrete individual detectors arranged in an integral unit using rotary motion only, and the use of multiple individual detectors minimizes count losses due to resolving time when a scintillation camera is used; also, data is collected at infinitely variable integral angles without any indexing dead-time, and without a need for reset and other adjustments between scan frames. The system also permits coincidence counting of annihilation radiation from position emitting radionuclides.

The continuous rotation permits continuous gathering of data over a long period of time with a subsequent determination of the time interval per frame. This gives an advantage in following dynamic processes, where previously the time per frame was predetermined. Also, the detector offset and interlacing obviates the requirement for linear detector translation. Additionally, the continuous 32 optical channel transmission provides continuous counting data, which are balanced by computer correction to normalize the responses of the individual detectors.

In this example, transverse scanning referred to as emission computerized tomography (CT) is provided using computer reconstruction of scan data to produce transverse section pictures of a brain by detecting gamma rays emitted from radioactive pharmaceuticals that have been administered to the patient for the purpose of brain study, and in particular protrayal of local brain function using cross-section pictures of brain radioactivity.

This is illustrated by the feature that in delayed brain scans, the differential brain concentration of radioactive pertechnetate usually reflects the integrity of the blood brain barrier for that substance, whereas earlier studies used emission CT scan to complement the basic four-view rectilinear study in selected patient's in order to clarify diagnosis. It was concluded that the double advantage of image separation and greater sensitivity of the section method of this invention improves the detection of tumors, especially those located in the basal regions of the brain, while the cross-section format gives superior description of lesion tomography, such as location, boundaries, multiplicity, and shape.

It is also understood from the above that the brain scanner of this invention combines the described transverse section scanning with the storage capabilities of the described conventional computer so as to store the scan data for later use in quantitatively regenerating and/or updating the scan at the physician's convenience, such that the speed, accuracy and memory of the computer are ideally suited for the analysis and display of the scanning data. Thus, the computer brings an enhanced dimension to the organization, presentation and perception of the scan data, which is continuously recorded and automatically loaded into the computer memory in such a way that the computer can superimpose the several scan lines to enhance the spatial and detailed resolution of deep-seated tumors in a flexible system having immediate display and instant replay, as well as accurate control for passing subsequent scan lines into the areas of suspicion, so that the physician can quickly decide whether additional scans are required before the patient is moved. This invention thus represents a further advance in integrating the flexibility of the mind and the eye of the physician with the rapid data analysis and display advantages of a computer.

The described tomographic transverse section radionuclide scanner provided by the described apparatus of this invention has the advantage of completely surrounding the scan field by enclosing it in one plane with a quadrangular array of detector assemblies so as to greatly increase the collection efficiency of the gamma photons with the attendant reduction of patient scanning time and the reduction of statistical fluctuation of the derived data over the systems known heretofore. To this end, this invention has the advantage of the continuous collection and processing of data in small time intervals corresponding to real time in the context of the relatively long time required for the prior single sequence collection and processing devices known heretofore. For example, the described apparatus scans the entire field in the 50 seconds required for 1 revolution, and the data processing and delivery of a desired display picture requires only 30 seconds; thereafter, a new picture, continuously growing in detail and continuously diminishing in noise content, appears every 50 seconds as the detector assemblies make one revolution. Furthermore, the quality of the data may be continuously monitored by the operator, and the scanning operation may be extended or curtailed thereby, in which case the quantitative datum may be produced on a standard computer printer.

What is claimed is:

1. Transverse section radionuclide scan field apparatus for use with an electronic system for the high-sensitivity quantification of brain radioactivity in cross-section picture format in order to permit accurate assessment of regional brain function localized in three-dimensions, the apparatus detecting high energy radiation emanating from sources at fixed locations in a human head, and the electronic system producing and displaying therefrom data that corresponds spatially with the location of the sources and quantatively with the intensity of the radiation emanating from the sources in a transverse plane, comprising:
   a. means communicating with the electronic system, comprising a system of high energy radiation detectors forming a continuous picture frame line of detectors that completely encloses the scan field in a plane for receiving and detecting said radiation from said sources and producing therefrom data corresponding spatially with the location of the sources and quantitatively with the intensity of the radiation emanating therefrom in a plane transverse to said head;
   b. means for rotating said detectors in unison as an integral unit in one direction around a single axis in a plane transverse to the head so as continuously to transmit data therefrom;
   c. said means for rotating said detectors rotating the same in a continuous, uninterrupted picture frame line of detectors that are tangent to the scan field and that completely enclose the same around the single axis to produce data corresponding to the spatial location and intensity of the sources; and
   d. electromagnetic means for transmitting to the electronic system the data produced by the detectors in response to the detection of the radiation thereby,
   the electromagnetic means for transmitting the data from the detectors, comprising laser-emitting photodiodes responsive to the detectors for producing data in the form of light pulses corresponding to the radiation detected.

2. The apparatus of claim 1 having electronic data collecting and transmitting means connected to the detectors to rotate therewith, the detectors being energized through and having a slip ring containing an optical data channel for receiving and transmitting the data collected via said laser-emitting photo-diodes.

3. The apparatus of claim 2 having control means connected to the electronic data collecting and transmitting means across said slip ring for continuously controlling said data collection and transmission via said optical data channel.

4. The apparatus of claim 2 including a computer system having a digital computer, an output printer and a display monitor for displaying the data collected and for controlling the apparatus continuously to scan the circumference of the head in one transverse plane, through 360° without detector translation in a plurality of separate planes.

5. Method for scanning a transverse plane of radionuclide sources in a system having detectors for detecting the decay products emanating from the sources for producing digital informational data corresponding to the spatial location and intensity of said sources, comprising the steps of:
   a. locating said detectors in a plane containing said sources;
   b. rotating said detectors continuously through 360°,
   c. the detectors being continuously rotated by driving the detectors to rotate in one direction around a single fixed axis normal to the mentioned plane at a predetermined angular velocity that exceeds 1 rpm;
   d. continuously transmitting the data produced by said detectors along said single fixed axis in a light beam that is pulsed at a frequency and an intensity corresponding to the data produced by the detectors; and
   e. continuously processing the data produced by the detectors to correlate the same with the spatial location and intensity of the sources.

* * * * *